United States Patent [19]  [11] 4,137,224
Taplin et al. [45] Jan. 30, 1979

[54] PROCESS FOR THE PREPARATION OF ANTIBIOTIC W-10 COMPLEX AND FOR THE ISOLATION OF ANTIBIOTIC 20561 AND ANTIBIOTIC 20562 THEREFROM

[75] Inventors: David Taplin, Miami, Fla.; Marvin J. Weinstein, East Brunswick, N.J.; Raymond T. Testa, Verona, N.J.; Joseph A. Marquez, Montclair, N.J.; Mahesh G. Patel, Verona, N.J.

[73] Assignee: Schering Corporation, Kenilworth, N.J.

[21] Appl. No.: 767,102

[22] Filed: Feb. 9, 1977

[51] Int. Cl.$^2$ .................... A61K 31/71; A61K 37/00; C07H 17/00
[52] U.S. Cl. .......................... 260/112.5 R; 195/31 R; 424/177; 424/181; 536/4; 536/17
[58] Field of Search ............... 536/17, 4; 260/112.5 R

[56] References Cited

U.S. PATENT DOCUMENTS

| 3,901,877 | 8/1975 | Kawaguchi et al. | 536/17 |
| 3,922,262 | 11/1975 | Umezawa et al. | 260/112.5 |

Primary Examiner—Johnnie R. Brown
Attorney, Agent, or Firm—Bruce M. Eisen; Raymond A. McDonald; Carver C. Joyner

[57] ABSTRACT

A novel antibiotic complex exhibiting antifungal activity is produced by fermenting a novel species of bacteria from the genus Aeromonas, the bacterium being herein designated Aeromonas sp, W-10. The antibiotic complex is comprised of at least three and possibly as many as six components and has been designated Antibiotic W-10 Complex. Two members of the complex have been isolated in substantially pure form and are designated Antibiotic 20561 and Antibiotic 20562, the antibiotics exhibiting substantial antifungal activity.

2 Claims, 2 Drawing Figures

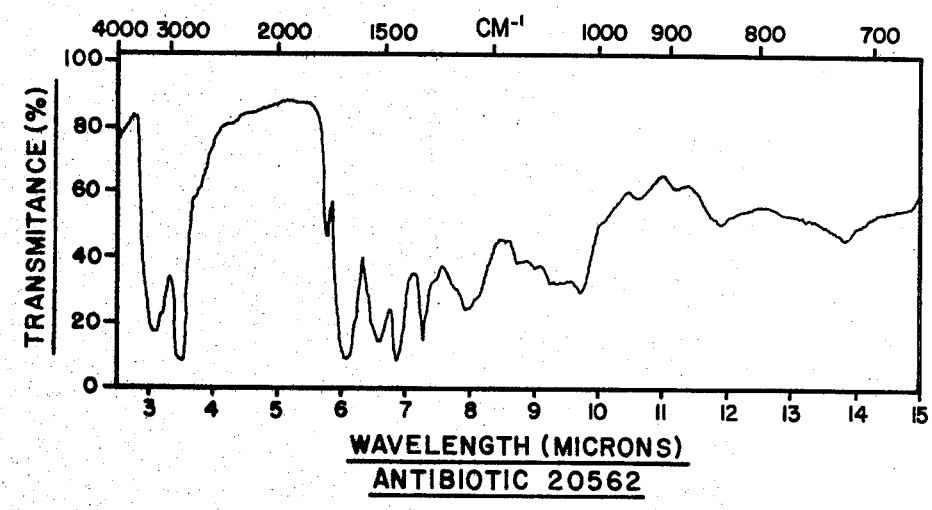
WAVELENGTH (MICRONS)
ANTIBIOTIC 20562
Fig_1
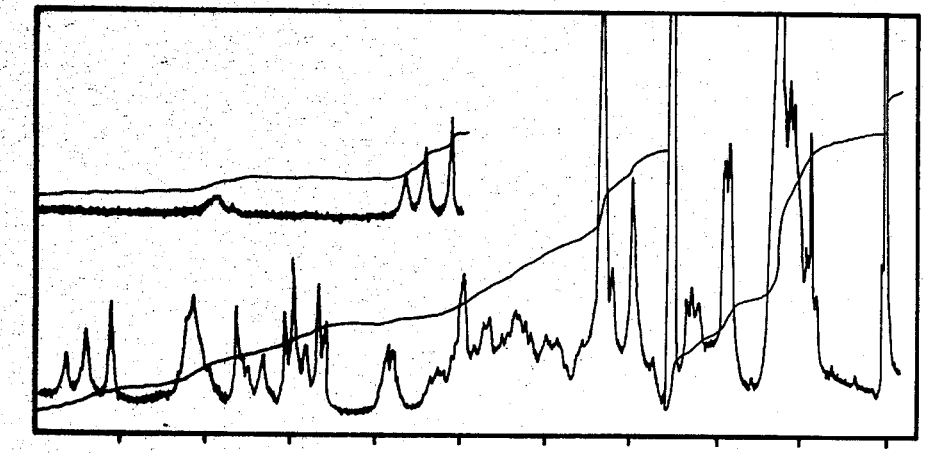
ANTIBIOTIC 20562
Fig_2

PROCESS FOR THE PREPARATION OF ANTIBIOTIC W-10 COMPLEX AND FOR THE ISOLATION OF ANTIBIOTIC 20561 AND ANTIBIOTIC 20562 THEREFROM

This invention relates to a novel bacterium and to an antifungal mixture produced thereby. More particularly, this invention relates to a bacterium of the genus Aeromonas, herein designated Aeromonas sp. W-10 and to the novel antibiotic mixture produced thereby.

THE MIXTURE

Cultivation of Aeromonas sp. W-10 under controlled aerobic conditions in an aqueous nutrient medium produces a mixture having antifungal activity. The mixture is herein designated "Antibiotic W-10 Complex". The complex consists of from three to about six discreet entities, two of which have been isolated free from the compounds coproduced therewith. These compounds exhibit substantial antifungal activity and are designated, "Antibiotic 20561" and "Antibiotic 20562".

Antibiotic 20561 is a solid composition of matter having the following physical properties:

(a) A melting point of 160° C.

(b) A specific optical rotation as measured at the D line of sodium at 26° C. of $-88° \pm 3°$ at 0.4% concentration in pyridine containing 5% water, and of $-66° \pm 2°$ in dimethylsulfoxide containing 5% water at 0.4% concentration;

(c) Ultraviolet absorption maxima in methanol at 220 and 280 m$\mu$ with $E_{1cm}^{1\%}$ of 313 and 20, respectively; and in methanol containing 10% v/v 1N sodium hydroxide, maxima are observed at 240 and 295 m$\mu$;

(d) A nuclear magnetic spectrum in deuterated dimethylsulfoxide — as set forth on page 17.

(e) An infrared absorption spectrum in mineral oil (Nujol) substantially as shown in Table IV;

(f) A molecular formula of $C_{57}H_{86}O_{16}N_{12}$; and having the following structural formula:

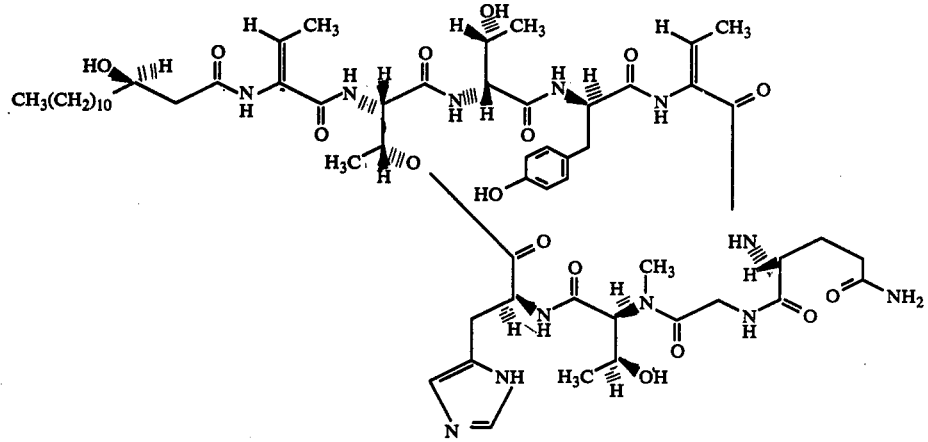

Antibiotic 20562 is a solid composition of matter having the following physical properties:

(a) A melting point of 170°–175° C.;

(b) A specified optical rotation as measured at the D line of sodium at 26° C. of $-60° \pm 3°$ in pyridine containing 5% water at 0.4% concentration, and is $-44° \pm 3°$ in dimethylformamide containing 5% water at 0.4% concentration;

(c) Ultraviolet absorption maxima in methanol at 222 and 280 m$\mu$ with $E_{1cm}^{1\%}$ of 268 and 14.8, respectively, and in methanol containing 10% v/v 1N sodium hydroxide, at 240 and 292 m$\mu$ with $E_{1cm}^{1\%}$ of 190 and 19.4, respectively;

(d) An infrared absorption spectrum in mineral oil (Nujol) substantially as shown in FIG. 1;

(e) A nuclear magnetic resonance spectrum in deuterated dimethylsulfoxide substantially as shown in FIG. 2;

(f) A molecular formula of $C_{63}H_{96}O_{21}N_{12}$; and having the following structural formula:

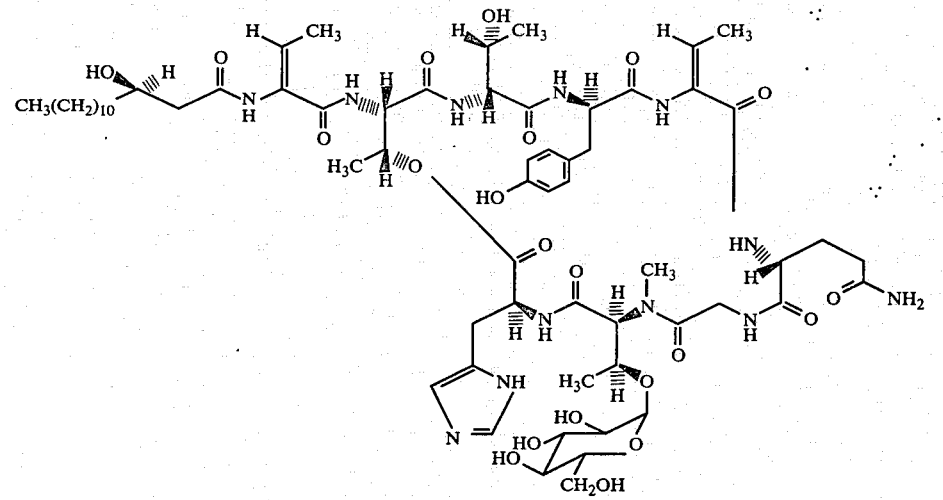

THE MICROORGANISM

Based upon the physiological characteristics, morphology and the guanine plus cytosine content of isolated DNA, we have classified the organism as a novel member of the genus Aeromonas. We have designated the bacterium Aeromonas sp. W-10, sometimes referred to herein as Aeromonas W-10, and have deposited the microorganism with the United States Department of Agriculture, Northern Utilization Research and Development Division (NRRL), Peoria, Illinois, from whom subcultures are available. The microorganism has been assigned the numerical designation NRRL B-11053. Although this invention is described in terms of Aeromonas sp. W-10, it is not limited to the particular strain on deposit but embraces Antibiotic W-10 producing mutants and variants obtained by the use of mutagenic agents, and by the use of methods known to the art such as exposing the microorganism to X-ray or ultraviolet radiation, or to nitrogen mustards, or to bacteriophages or the like. When observed microscopically, Aeromonas sp. W-10 is seen to be a non-spore forming, gram-negative rod approximately 0.5 to 1.0 × 1.0–1.5 microns. It occurs singly and is motile by means of a single polar flagellum. The organism is facultatively anaerobic, oxidase positive, capable of reducing nitrates to nitrites, insensitive to the vibriostatic compound 2,4-diamino-6,7-diisopropylpteridine (0/129) with a guanine-cytosine content of DNA at 61%. According to Bergy's Manual of Determinative Bacteriology, 8th Edition, the organism is, on the basis of the data set forth, classified as a member of the genus Aeromonas.

The growth and physiological characteristics of Aeromonas sp. W-10 on various media are presented in the following tables. All observations were made after seven (7) days of incubation at 28° C. Color designations are assigned according to the classification in the Color Harmony Manual (1958), Container Corporation of America. The designates G, S, C and R used herein stand for growth, surface, color and reaction, respectively.

Table I

| Growth Characteristics of Aermonoas sp. W-10 on Various Media | |
|---|---|
| Medium | Description |
| Bennett's Agar | G: +++, good |

Table I-continued

| Growth Characteristics of Aermonoas sp. W-10 on Various Media | |
|---|---|
| Medium | Description |
| | S: flat, no aerial mycelium; no diffusable pigment |
| | C: g4pg, dark luggage tan |
| Calcium Citrate Agar | G: +, fair |
| | S: plicate, no aerial mycelium; no diffusable pigment |
| | C: g3ic, light amber |
| Calcium Malate Agar | G: +, fair |
| | S: plicate, no aerial mycelium; no diffusable pigment |
| | C: g 1½ Ca, cream |
| Czapek's Glucose Solution | G: ±, poor |
| Czapek's Sucrose Agar | G: ±, poor |
| Emerson's Agar | G: +++, good |
| | S: flat to plicate, no aerial mycelium; no diffusable pigment |
| | C: g3ec, light beige |
| Glucose - Asparagine Agar | G: ++, moderate |
| | S: flat, no aerial mycelium; no diffusable pigment |
| | C: g2eg, beige |
| Glucose - Yeast Extract Agar | G: +++, good |
| | S: flat to plicate, no aerial mycelium; no diffusable pigment |
| | C: center g3ec, light beige periphery - g4pe, orange rust |
| Nutrient Agar | G: +, fair |
| | S: flat, no aerial mycelium; no diffusable pigment |
| | C: g2ne, luggage tan |
| NZ Amine Glucose Agar | G: +++, good |
| | S: flat to plicate, no aerial mycelium |
| | C: center - g4ng, saddle tan periphery - g3ec, light beige |
| Ordinary Agar | G: ±, poor |
| Peptone Glucose Agar | G: +++, good |
| | S: plicate, no aerial mycelium; no diffusable pigment |
| | C: g4ne, luggage tan |
| Potato Slice | G: +++, good |
| | S: flat, no aerial mycelium; no diffusable pigment |
| | C: g3ie, camel |
| Starch Agar (Waksman No. 21) | G: ±, poor |
| Tomato Paste Oatmeal Agar | G: +++, good |
| | S: flat to plicate, no aerial mycelium; no diffusable pigment |
| | C: g4pg, dark luggage tan |

Table III

Physiological Characteristics of Aeromonas sp. W-10

| Test | Result | Test | Result |
|---|---|---|---|
| Acid Production[1] From: | | | |
| Adonitol | − | Fermentation of: | |
| D-Arabinose | − | Glucose | + |
| L-Arabinose | − | | |
| Cellibiose | − | Hydrolysis of: | |
| Dextrin | + | Gelatin | + |
| Dulcitol | − | Casein | + |
| Erythritol | − | Starch | ± (weak) |
| | | Egg | − |
| Fructose | + | Serum | + |
| Galactose | − | Cellulose | −→± |
| Glucose | + | Tyrosine | + |
| Glycerol | + | Reactions: | |
| Glycogen | + | Litmus Milk | Coagulation, slight peptonization |
| Inositol | + | | |
| Inulin | + | | |
| Lactose | − | Nitrate to | |
| Maltose | − | Nitrite | positive |
| Mannitol | + | | |
| Mannose | − | Indole | − |
| Melibiose | − | Catalase | + |
| Raffinose | − | Oxidase | + |
| Rhamnose | − | Arginine | |
| Ribose | − | Hydrolase | + |
| Sorbitol | − | Lysine | |
| Sucrose | − | Decarboxylase | − |
| Trehalose | − | Ornithine | |
| D-xylose | − | Decarboxylase | − |
| | | Urease | − |
| | | Growth At: | |
| | | pH 6 | + |
| | | 28 C | + |
| | | 37 C | ±→+ |
| | | 45 C | − |
| | | Production of: | |
| | | H₂S | − |
| | | Melanin | − |
| Resistance to: | | | |
| 0/129 (300 mcg) | + | NaCl Tolerance: | 2–3% |
| Polymyxin (50 mcg) | + | | |
| Penicillin G (10 u) | + | Diaminopimelic Acid | |
| Bacitracin (10 u) | + | in whole cells | +(meso) |
| Gentamicin (10 mcg) | − | | |
| Sisomicin (10 mcg) | − | | |
| Naladixic Acid (50 mcg) | − | % Guanine-Cytosine | 61% ± 2% |

[1]Gas not formed in the aerobic breakdown of carbohydrates.

Table II

Growth characteristics and physiological properties of Aeromonas W-10 on various media

| Medium | Description |
|---|---|
| Egg Agar (Dorset's) | G: ++, moderate |
| | S: flat, no aerial mycelium; no diffusable pigment |
| | C: g2ca, ivory |
| | R: no hydrolysis - negative |
| Loeffler's Serum Medium | G: +++, good |
| | S: flat, no aerial mycelium; no diffusable pigment |
| | C: g3ie, camel |
| | R: Serum partially liquified - positive |
| Gelatin Agar (McDade) | G: +++, good |
| | S: plicate, no aerial mycelium; no diffusable pigment |
| | C: g3ie, camel |
| | R: Gelatin hydrolyzed - positive |
| Starch Agar | G: +++, good |
| | S: flat, no aerial mycelium, no diffusable pigment |
| | C: g3ec, light beige |
| | R: Starch weakly hydrolyzed |
| Tyrosine Yeast Agar | G: +++, good |
| | S: plicate, no aerial mycelium, no diffusable pigment |
| | C: g3pi, tobacco brown |
| | R: Tyrosine crystals dissolved - positive |
| Tyrosine Beef Agar | G: +, fair |
| | S: flat, no aerial mycelium, no diffusable pigment |
| | C: g3ec, light beige |
| | R: Tyrosine crystals dissolved - positive |

THE FERMENTATION

Although Aeromonas sp. W-10 will grow on a wide variety of nutrients, the following are preferred for preparing the vegetative inoculum: trypticase, soy peptone, beef infusion, casamino acids, dextrose, soluble starch and inorganic salts such as sodium chloride and dipotassium phosphate.

Similarly, Aeromonas sp. W-10 will produce the Antibiotic W-10 Complex in a nutrient medium containing any of a wide variety of nutrients. However, the following are preferred: casamino acids, soluble starch, soybean meal, dextrose, buffers e.g. calcium carbonate and inorganic salts, such as cobalt chloride.

The production of Antibiotic W-10 Complex is commenced by the preparation of a vegetative inoculum of Aeromonas sp. W-10 in a suitable nutrient medium from an agar slant or of a portion of a frozen broth culture. The nutrient medium is a conventional one containing assimilable sources of nitrogen and carbon and is usually inoculated with a 5% v/v transfer of frozen broth culture. The inoculum preparation is preferably effected at a temperature in the vicinity of 35° C. for from about 24 to about 48 hours with aeration and agitation. For production-sized fermentations, a second inoculum preparation is recommended.

The fermentation may be effected in a medium having the same constituents as the inoculum medium or in one containing different nutrients and is preferably effected at a temperature in the vicinity of 28°, a pH of about 6.5-7.0 using a 5% v/v inoculum. The fermentation is complete in from about 48 to about 90 hours, usually from about 48 to about 72 hours with aeration and agitation.

Peak Antibiotic W-10 Complex production is determined by periodic sampling of the fermentation mixture and by subjecting the samples to an agar diffusion assay using *Saccharomyces cerevisiae* ATCC 9763 as the test organism. The broths are assayed against a standard solution of Antibiotic 20562 having an assigned potency of 1000 mcg/mg. The standard solution is diluted with 10% potassium phosphate buffer (pH 6.0) to make solutions having antibiotic concentrations of 3.2, 4.0, 5.0, 6.25 and 7.8 mcg/ml. The assay is performed substantially as set forth in the Federal Register, Title 21, Chapter 436.105.

THE ANTIBIOTICS

When peak Antibiotic W-10 Complex activity is attained, the fermentation mixture is extracted with a polar water immiscible organic solvent, preferably butanol saturated with water. The extracts are combined and concentrated, preferably in vacuo until a precipitate forms wherein the suspension is filtered. The filtrate is concentrated to a residue, redissolved in methanol and added to a 1:1 mixture of petroleum ether; ethyl ether with agitation. The resulting precipitate is removed by filtration and dried in vacuo. The precipitate removed during the concentration of the butanol extracts and the residue obtained by concentration of the filtrate both contain Antibiotic 20561, Antibiotic 20562 in admixture with biologically inactive organic matter and the other unidentified active substances forming the Antibiotic W-10 Complex. Separation of Antibiotic 20561 and Antibiotic 20562 is best accomplished by chromatographic means after a suitable pre-treatment to remove grossly different materials.

The pre-treatment consists of dissolving the solids in a suitable solvent, e.g. methanol treating the resulting solution with activated charcoal, or other color-removing substances, and filtering. The partially purified Antibiotic W-10 Complex is then precipitated by addition of the filtrate to a (1:1) petroleum ether:ethyl ether mixture. The resulting precipitate is chromatographed on a silica gel column using a chloroform:methanol (1:1) solvent mixture as the eluent.

The separation is monitored by sampling the column effluent, chromatographing the samples by thin layer chromatography preferably using Gelman I.T.L.C (SA), silicic acid as the adsorbent and chloroform, methanol and water (50:50:4) as the solvent system. After detection of the antibiotics in each sample, fractions containing materials having Rf of 0.66 (0.56-0.72) are combined as are the materials having an Rf of 0.32 (0.30-0.35). On conventional silica gel plates (i.e. Analtech® TLC plates) pure samples of Antibiotic 20561 and Antibiotic 20562 have Rf values of 0.63 and 0.19, respectively, when chromatographed in the solvent system consisting of chloroform: methanol: ammonium hydroxide: water 60:30:3:2. Detection of the antibiotic is antibiotic accomplished by exposure of the chromatogram to iodine vapors wherein the antibiotic appears as a dark spot or spots against a white background. Detection is also accomplished by placing the thin layer sheet upon an agar plate seeded with *Saccharomyces cerevisiae*, incubating the plate for about 16-18 hours and measuring the location of the zone or zones of inhibition. In this manner, Antibiotic 20561 and Antibiotic 20562 are separated from the substances co-produced therewith and may be obtained as crystalline solids from methanol. Antibiotics 20561 and 20562 have the physical constants and structural formulae set forth above. They assay about 800 and about 1000 mcg/mg., respectively, according to the assay previously described.

INFRARED

The infrared spectrum set forth in FIG. 1 is that of Antibiotic 20562 which used a Perkin-Elmer IR 221 Spectrophotometer with a sodium chloride prism and was obtained on a sample of Antibiotic 20562 in the form of a mineral oil (Nujol) mull. The characteristic absorption bands [as Wave-Numbers (W-N) in $Cm^{-1}$] of Antibiotic 20561 and of Antibiotic 20562 are as follows:

Notations: v.str. — very strong, str. — strong, m. — medium, w. — weak, v.w. — very weak, br. — broad, s. — sharp, sh. — shoulder

TABLE IV

| ANTIBIOTIC 20561 | | | | ANTIBIOTIC 20562 | | | |
|---|---|---|---|---|---|---|---|
| W-N ($Cm^{-1}$) | Notation | W-N ($Cm^{-1}$) | Notation | W-N ($Cm^{-1}$) | Notation | W-N ($Cm^{-1}$) | Notation |
| 3300 | m.,br. | 1380 | Nujol | 3226 | str.,br. | 1105 | w. |
| 2960-2860 | Nujol | 1255 | m. | 2946-2817 | Nujol | 1080 | w. |
| 1740 | w. | 1065 | w. | 1736 | m.,str. | 1064 | w. |
| 1655 | str. | 840 | w. | 1667-1626 | v.str.,br. | 1026 | w. |
| 1520 | str. | 720 | w. | 1546 | sh. | 990 | sh. |
| 1460 | Nujol | | | 1522 | str.,br. | 935 | v.w. |
| | | | | 1460,1377 | Nujol | 889 | v.w. |
| | | | | 1266-1235 | m.,br. | 837 | w.,v.br |
| | | | | 1143 | w. | 722 | w.,v.br. |

NUCLEAR MAGNETIC RESONANCE (NMR), SPECTRAL WIDTH - 1000 Hz

Antibiotic 20562 has a characteristic NMR spectrum as shown by FIG. 2. The spectrum was obtained using a Varian XL-1 100-15 spectrometer and a Varian 620L-100 disk-based computer (Varian Associates, 611 Hansen Way, Palo Alto, California). Tetramethylsilane was used as the internal standard and the sample was dissolved in deuterated dimethylsulfoxide (DMSO $d_6$). For structural determination, the following absorption peaks are characteristic: (in p.p.m. from TMS), 0.87, 3H, triplet (J = 7 Hz), $CH_3$—$CH_2$—; 1.15-0.96, 9H, overlapping doublet (J = 5 Hz), CH₃—CHCH—; 1.25, 2OH, —(CH₂)₁₀—, 1.86, 6H, doublet (J = 7 Hz),

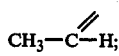

2.98, 3H, CH₃—N <; 5.82, 2H, 2 overlapping quartets (J = 7 Hz),

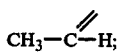

$$\left.\begin{array}{r}6.61\\7.01\end{array}\right\}$$

4H, doublets (J = 8 Hz),

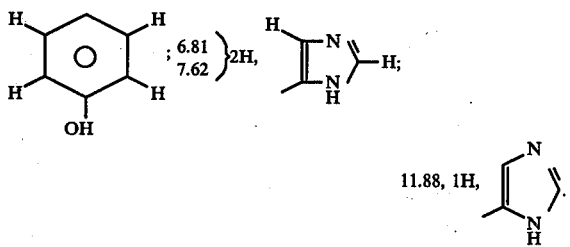

In a similar manner, when the NMR spectrum of Antibiotic 20561 is obtained by use of the same spectrometer and under the same conditions, the following peaks are found to be characteristic:

0.85, 3H, triplet (J = 7 Hz), CH₃—CH₂—; 0.98–1.09, 9H, overlapping doublet (J = 5 Hz), CH₃CH(O—)—; 1.21, 2OH, —(CH₂)₁₀—; 1.80, 6H, doublet (J = 7 Hz), CH₃—CH ═; 2.84, 3H, CH₃—N <.

BIOLOGICAL ACTIVITY OF ANTIBIOTIC 20562

In Vitro

Antibiotic 20562 was tested in vitro in Sabourraud dextrose broth against strains of *Candida albicans*, the Minimum Inhibitory Concentration (MIC) being set forth in Table IV below:

Table V

| Strains of Candida albicans | MIC (mcg/ml) |
|---|---|
| Burke | 0.075 |
| Lush | 0.075 |
| Fix | 0.075 |
| Collins | 0.075 |
| Merkel | 0.075 |
| 29 | 0.075 |
| Raub | 0.075 |
| Sperk | 0.075 |
| Bevan | 0.075 |
| Newcomb | 0.075 |
| Wisconsin | 0.075 |
| No. 1 | 0.075 |

BIOLOGICAL ACTIVITY OF ANTIBIOTIC 20561 AND ANTIBIOTIC 20562

In Vivo

The in vivo activity of Antibiotic 20561, Antibiotic 20562 and the Antibiotic W-10 complex are obtained using male CF1 mice (Carworth Famrs) given a single oral or subcutaneous dose one hour after intraveneous infection with sufficient *Candida albicans* to kill 80% of the infected mice in 48 hours.

PD₅₀ values were determined 48 hours after infection and are as follows:

Antibiotic 20561 subcutaneous administration PD₅₀ = 4 mg/kg; oral administration; PD₅₀ = 25 mg/kg. Antibiotic 20562 subcutaneous administration; PD₅₀ = 4 mg/kg; oral administration; PD₅₀ = 25 mg/kg. Under the same test conditions Antibiotic W-10 Complex via both oral and subcutaneous administration had a PD₅₀ = 4 mg/kg.

Toxicity

Antibiotic W-10 Complex upon oral or subcutaneous administration, exhibited an LD₅₀ greater than 50 mg/kg. Antibiotic 20561 and Antibiotic 20562 under the same test conditions exhibited an LD₅₀ of > 1000 and 600 mg/kg., respectively, via subcutaneous administration and 1000 and 800 mg/kg., respectively, via oral administration.

Topical in vivo Activity of Antibiotic 20562 Against Candida Albicans Intravaginal Infection in Hamsters Test Procedure Using a culture of *Candida albicans* (Wisconsin strain), in Sabourrauds dextrose broth, infect intravaginally, five groups of six female hamsters. Forty-eight and seventy-two hours after infection, make smears of the infected animals and culture the smears. Forty-eight hours later (96 hours after infection), make additional smears, culture and commence treatment. One group of six animals (controls) receives no treatment and, therefore, remains infected throughout the test. The remaining four groups of animals are treated with Antibiotic 20562, as 1%, 5%, 10% and 15% suspensions, respectively, the vehicle for suspension being administered on a cotton swab. At the end of the three day treatment the 1%, 5% and 10% groups are 60% cured, the 15% group is completely (100%) cured.

In vivo Activity of Antibiotic 20561 and Antibiotic 20562 Against Trichophyton Mentagrophytes Infection in Guinea Pigs The skin of fifteen guinea pigs is abraded and infected with a standard culture of *Trichophyton mentagrophytes*. The infected animals are then separated into three groups containing five animals each. Suspensions containing 1% of the respective antibiotics in polyethylene glycol 400 are prepared. Two of the three groups are treated topically, twice daily for ten days commencing three days after infection. The third group (controls) remained untreated throughout the test. All of the animals are tested for infection by culture and observed for skin lesions for a total of 21 days. The test results are as follows:

| Compound | Days to become negative Culture | Lesion |
|---|---|---|
| Antibiotic 20561 | 4.8 | 6.3 |
| Antibiotic 20562 | 5.8 | 9.0 |
| Controls | >22 | >22 |

The novel antibiotics of this invention, i.e. Antibiotic W-10 Complex, Antibiotic 20561 and Antibiotic 20562, are preferably administered topically, but may be administered orally or parenterally and, preferably, in admixture with a pharmaceutically acceptable carrier or excipient. The precise dose to be administered in any particular dosage form will depend upon such factors as the stage and severity of the infection, the susceptibility of the infecting organism to the antibiotic and the individual characteristics of the animal species being treated. However, in general when the compounds of this invention are administered parenterally, dosages in the range of 1 mg. to 10 mg. per kg. per day are given, usually in divided doses up to four times a day.

For topical administration, liquid suspensions, creams or ointments of 0.1% to 5% by weight are used usually as a single application each day.

For oral administration, the compounds of this invention are used in the form of elixirs, tablets, capsules or the like. Dosages of 1 mg. to 5 mg. per kg. are administered, usually in divided doses up to four times a day. The following are exemplary of the dosage forms in which Antibiotic W-10 Complex, Antibiotic 20561 and Antibiotic 20562 may be employed, notwithstanding the fact that for a given dosage form, only one of the above-named antibiotics is specifically designated.

CAPSULE

| Ingredients | mg/capsule | mg/capsule |
|---|---|---|
| Antibiotic 20562, micronized | 35 | 175 |
| Sodium Lauryl Sulfate, USP | 5 | 25 |
| Lactose, Hydrous (USP Impalpable Powder) | 318 | 158 |
| Corn Starch (Food Grade) | 40 | 40 |
| Magnesium Stearate, USP | 2 | 2 |
| | 400 mg | 400 mg |

Procedure

Mix the first four (4) above-named ingredients in a suitable blender for 5–10 minutes. Pass the mixture through a No. 30 mesh screen and re-blend for 5 minutes. Premix the magnesium stearate with a portion of the blended material, add the premix to the main batch and blend for 1–3 minutes. Fill the blended powder into two-piece, hard gelatin capsules using a suitable encapsulating machine.

TABLET

| Ingredients | mg/tablet | mg/tablet |
|---|---|---|
| Antibiotic 20562, micronized | 35.0 | 175.0 |
| Sodium Lauryl Sulfate, USP | 5.0 | 25.0 |
| Lactose, USP | 307.5 | 147.5 |
| Microcrystalline Cellulose NF | 50.0 | 50.0 |
| Corn Starch (Food Grade) | 50.0 | 50.0 |
| Polyvinylpyrrolidone (20% aqueous solution) | 50.0 | 50.0 |
| Magnesium Stearate, USP | 2.5 | 2.5 |
| | 500.0 mg | 500.0 mg |

Procedure

Mix the first five (5) above-named ingredients in a suitable blender for 10–15 minutes. Granulate the mixture with the polyvinylpyrrolidone until a uniform damp mass is formed, (add additional water, if necessary). Pass the damp mass through a No. 8 mesh screen. Spread the damp granules on trays and dry overnight between 40° – 50° C. Mill the dried granules using a suitable mill with a No. 16 mesh screen. Add the magnesium stearate to the milled granules and mix for 1 – 3 minutes. Compress the mixture to the specified weight (i. e., 500 mg.) on a suitable tablet press.

PARENTERAL DOSAGE

| Ingredients | mg/ml |
|---|---|
| Antibiotic 20562 | 200 |
| Propylene Glycol | 400 |
| Glycine | 100 |
| Tween 80 | 5 |
| Sodium Hydroxide 0.1 N or Hydrochloric Acid 0.1 N | qs to pH 7.0 |
| Water for injection | qs to 1.0 ml |

Procedure

Add the antibiotic as a sterile powder, to a mixture of the remaining ingredients. Adjust the pH to 7.0 using the sodium hydroxide or the hydrochloric acid, as required. Filter the formulation through a 0.22 μ membrane and aseptically fill into ampules of vials.

Alternate Procedure

Sterilize Antibiotic 20562 using ethylene oxide, or sterile filtration, or lyophilization. Transfer under aseptic conditions 200 mg of Antibiotic 20562 to each of a plurality of vials. Mix the remaining ingredients as set forth in the procedure above and sterilize by filtration through a 0.22 μ membrane. Under aseptic conditions fill into the vials containing the antibiotic.

TOPICAL COMPOSITION

CREAM

| Ingredients | mg/g | mg/g |
|---|---|---|
| Antibiotic 20562, micronized | 10.00 | 50.00 |
| 4-Chloro-m-Cresol | 2.00 | 2.00 |
| Sodium Phosphate Monobasic Monohydrate | 2.65 | 2.65 |
| Phosphoric Acid, NF | 0.02 | 0.02 |
| White Petrolatum, USP | 150.00 | 110.00 |
| Mineral Oil, USP(75 centistokes) | 60.00 | 60.00 |
| Polyethyleneglycol 1000 monocetyl ether | 22.50 | 22.50 |
| Cetostearyl Alcohol | 72.00 | 72.00 |
| Water, USP qs to | 1.00g | 1.00g |

Procedure

Heat the mineral oil, white petrolatum cetostearyl alcohol and a portion of the polyethyleneglycol 1000 monocetyl ether to 70° C., with agitation. In another vessel, heat about 90% of the water to 70° C., with agitation and add the 4-chloro-m-cresol, sodium phosphate and the phosphoric acid. Add the oil (mineral oil, etc.) phase to the aqueous phase at 70° C., with vigorous agitation. Cool to 60° C., with vigorous agitation, then to 38° C., with gentle agitation. Dissolve the remaining Polyethylene glycol 1000 monocetyl ether in water at 65° C., cool to 35° C., add Antibiotic 20562 with agitation. Add the antibiotic suspension to the cream base at 35° C. with moderate agitation and cool to room temperature (20° C.–25° C.).

TOPICAL COMPOSITION

OINTMENT

| Ingredients | mg/g | mg/g |
|---|---|---|
| Antibiotic 20561, micronized | 10.00 | 10.00 |
| Mineral Oil, USP (75 centistokes) | 50.00 | 50.00 |
| White Petrolatum, USP to make | 1.00g | 1.00g |

Procedure

Heat a weighed portion of white petrolatum and mineral oil to 65° C. while mixing. Cool the mixture to 50°-55° C. with stirring. Disperse the Antibiotic 20561 in the remainder of the mineral oil and mill. Add the antibiotic suspension to the petrolatum-mineral oil mixture with stirring, add the remainder of the petrolatum and cool to room temperature (20°-25° C.).

Solution

| | | |
|---|---|---|
| Antibiotic 20562 | | 0.2% W/V |
| N-Methyl-2-Pyrrolidone | | 20.0% W/V |
| Isopropyl-Myristate | | 5.0% W/V |
| Methanol | q.s. ad | 100.0% |

Procedure

Dissolve the antibiotic in the N-methyl-2-pyrrolidone, add the isopropyl myristate and adjust to the desired volume with methanol.

Gel

| | | |
|---|---|---|
| Antibiotic 20562 | | 0.2% W/W |
| N-Methyl-2-Pyrrolidone | | 70.0% W/W |
| Carbomer-934 | | 1.0% W/W |
| Methanol | | 10.0% W/W |
| Sodium Hydroxide 1.0N q.s. pH | | 5-6 |
| Purified Water | q.s. ad | 100.0% |

Procedure

Dissolve the antibiotic in the N-methyl-2-pyrrolidone, add methanol and water to 90% of final weight. Adjust the pH to 5-6 with the sodium hydroxide and adjust weight to 90% of final weight. Add the carbomer-934 using high speed agitation to facilitate gel formation.

CREAM

| | |
|---|---|
| Antibiotic 20562 | 0.2% W/W |
| N-Methyl-2-Pyrrolidone | 20.0% W/W |
| Sorbitan Monostearate | 2.0% W/W |
| Polyoxyethylene Sorbitan Monostearate | 1.5% |
| Methanol | 10.0% |
| Cetopalmitate Wax | 3.0% |
| Cetostearyl Alcohol | 10.0% |
| 2-Octyl Dodecanol | 13.5% |
| Benzyl Alcohol | 11.0% |
| Purified Water q.s. ad | 100.0% |

Procedure

Dissolve the antibiotic in the N-methyl-2-pyrrolidone and 90% of the required water. Heat the solution to 70° C. Heat the sorbitan monostearate, polyoxyethylene sorbitan monostearate, cetopalmitate wax, cetostearyl alcohol and 2-octyl dodecanol to 70° C. in a separate vessel and add the mixture to the antibiotic solution at 70° C. with rapid agitation. Cool the mixture to 45° C., then add the methanol and benzyl alcohol. Cool to 20° C. and adjust to the final weight with water.

PREPARATION OF STOCK CULTURE AEROMONAS sp. W-10

Dissolve 30g of trypticase soy broth medium solids (Baltimore Biological Laboratories (BBL), Cockeysville, Maryland) in 1.0 liter of water and sterilize. Inoculate the sterile medium with a loopful of Aeromonas sp. W-10 from an agar slant. Incubate the inoculated medium at about 35° C. for 24-48 hours with continual agitation. Freeze the culture for later use.

In a similar manner, a suitable culture may be prepared using 22g Mueller-Hinton broth medium solids (BBL), in 1.0 liter of water, followed by sterilization, inoculation and growth.

EXAMPLE 1

Preparation of Antibiotic W-10 Complex

A. Inoculum Preparation

Dissolve 30g of trypticase soy broth solids (BBL), in 1.0 liter of tap water and sterilize. Add 100 ml of Aeromonas sp. W-10 stock culture and incubate with agitation for 36 hours at 35° C.

B. Fermentation

Suspend the following ingredients in 10 liters of tap water in a 14 liter fermentor and sterilize: Dextrin-500g, soybean mean, 350g, calcium carbonate 70g, dextrose 50g and cobalt chloride 2.4mg. Inoculate the medium with 500 ml of the inoculum prepared in Step A. Incubate at about 28° C. and at pH 6.5-7.0 with agitation of about 300 rpm and aeration at about 3.0 liters/minute. Commence assaying the broth after about 24 hours and continue the fermentation until peak activity is attained.

C. Isolation of Antibiotic W-10 Complex

Pool the contents of 4 ten liter fermentors which have reached peak activity and extract twice using 2 volumes (80-120 liters) of butanol saturated with water. Combine the extracts and concentrate to a residue. Filter the precipitate which usually forms during the concentration and set aside. Dissolve the residue in methanol and precipitate into a 1:1 mixture of ethyl ether-petroleum ether. Dry the precipitate to obtain thereby Antibiotic W-10 Complex in admixture with biologically inactive materials.

Yield - 29g. Assay 75 mcg/mg

EXAMPLE 2

Isolation of Antibiotic 20561 and of Antibiotic 20562

A. Partial Purification of Antibiotic W-10 Complex

Dissolve 29g of Antibiotic W-Complex in 300 ml of methanol and treat with 50g of activated carbon for one hour, (e.g. Darco G60, Atlas Powder Co., Wilmington, Delaware). Filter the suspension, concentrate the filtrate and precipitate the antibiotic complex with a 1:1 petroleum ether-ethyl ether mixture. Dry the precipitate to obtain thereby Antibiotic W-10 Complex.

Yield -8.0g. Assay 200 mcg/mg

B. Chromatography of Antibiotic W-10 Complex

Prepare a silica gel chromatographic colum having the dimensions 10cm × 60cm and charge 8.0g of Antibiotic W-10 Complex to the column. Elute the column with a chloroform-methanol 1:1 solvent mixture at the flow rate of 0.5ml/min. Collect 20ml fractions while monitoring the column by thin layer chromatgraophy using a chloroform:methan:water (50:50:4) solvent system followed by bioautography. Pool the fractions having an Rf of 0.66 (0.56-0.72) and also pool the fractions having an Rf of 0.32 (0.30-0.35). Concentrate the pool resulting from the less polar fractions to a residue, dissolve the residue in methanol and precipitate with a 1:1 petroleum ether, ethyl-ether mixture. Dry the precipitate in vacuo at 40° C. to obtain thereby 415 mg of Antibiotic 20561; assay 800 mcg/mg.

Concentrate the combined more polar fractions, i.e. those having an Rf of 0.32 (0.30–0.35) and treat as described immediately above to obtain 600 mg of Antibiotic 20562; assay 800 mcg/mg.

The foregoing antibiotics, i.e. Antibiotic 20561 and Antibiotic 20562 may be further purified by crystallization from methanol.

EXAMPLE 3

Alternate Isolation of Antibiotic 20561 and Antibiotic 20562.

A. Isolation of Antibiotic W-10 Complex

Pool the contents of 6 ten liter fermentors which have reached peak activity and extract twice using 2 volumes of butanol saturated with water. combine the extracts and concentrate until a precipitate is formed. Cool the suspension and filter. Dry the precipitate to obtain thereby Antibiotic W-10 Complex plus biologically inactive material.

Yield - 29g

B. Partial purification of Antibiotic W-10 Complex

Dissolve the product from step A in 300 ml of methanol and treat with 50g of activated carbon for one hour (e.g. Darco G60, Atlas Powder Co., Wilmington, Del.). Filter the suspension, concentrate the filtrate and precipitate the antibiotic complex with a 1:1 petroleum ether-ethyl ether mixture. Dry the precipitate to obtain thereby Antibiotic W-10 Complex.

Yield - 4.0g

C. Isolation of Antibiotic 20561

Chromatograph the 4.0g of Antibiotic W-10 Complex as described in Example 2, step B. Combine the fractions having an Rf of 0.66 (0.56–0.72). Concentrate to a residue, dissolve the concentrate in methanol and precipitate with a 1:1 mixture of petroleum ether and ethyl ether.

Yield - 90 mg. Assay 800 mcg/mg
M.P. 160°–166° C.
$[\alpha]_D^{26} + -88°$ (95% pyridine, 5% H$_2$O; C = 0.4)

D. Isolation of Antibiotic 20562

Combine the fractions having an Rf of 0.32 (0.30–0.35), concentrate the pooled fractions to a residue and proceed as described immediately above to obtain the product of this step.

Yield - 400 mg. Assay 1000 mcg/mg
M.P. 170°–175° C.
$[\alpha]_D^{26} = -60°$ (95% pyridine, 5% H$_2$O; C = 0.4)

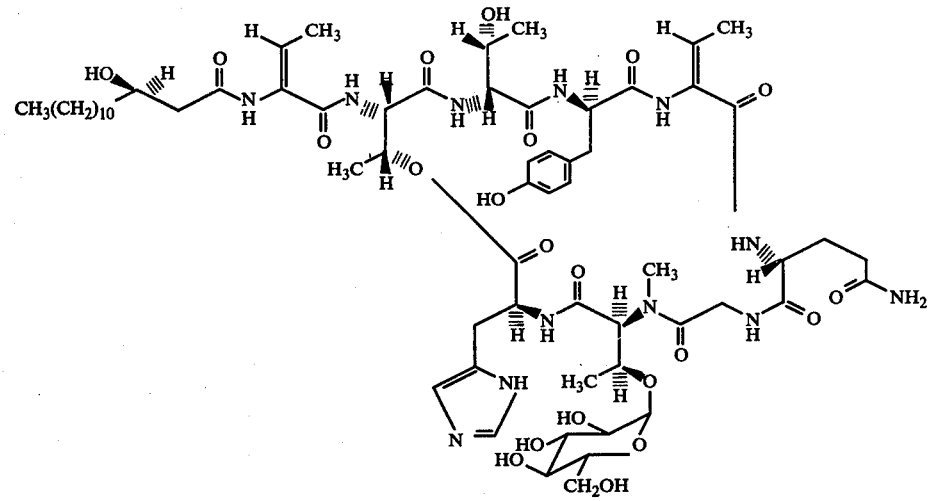

We claim:

1. Antibiotic 20561, said antibiotic having the following physical properties:
   (a) A melting point of 160°–166° C.;
   (b) A specific optical rotation as measured at the D line of sodium at 26° C. of $-88° \pm 3°$ at 0.4% concentration in pyridine containing 5% water and of $-66° \pm 2°$ at 4% concentration in dimethylsulfoxide containing 5% water;
   (c) Ultraviolet absorption maxima in methanol at 220 and 280 mμ with $E_{1cm}^{1\%}$ of 313 and 20, respectively; and in methanol containing 10% v/v 1N sodium hydroxide, maxima are observed at 240 and 295 mμ;
   (d) A nuclear magnetic spectrum in deuterated dimethylsulfoxide containing the following characteristic absorption peaks in parts per million form tetramethylsilane (TMS):
   0.85, 3H, triplet (J = 7 Hz), CH$_3$—CH$_2$—; 0.98–1.09, 9H, overlapping doublet (J = 5 Hz), CH$_3$—CH(O—); 1.21, 20H, —(CH$_2$)$_{10}$—; 1.80, 6H, doublet (J = 7 Hz), CH$_3$—CH=; 2.84, 3H, CH$_3$—N<.
   (e) An infrared absorption spectrum in mineral oil (Nujol) substantially as shown in Table IV;
   (f) A molecular formula of C$_{57}$H$_{86}$O$_{16}$N$_{12}$;
   (g) And having a structural formula substantially as follows:

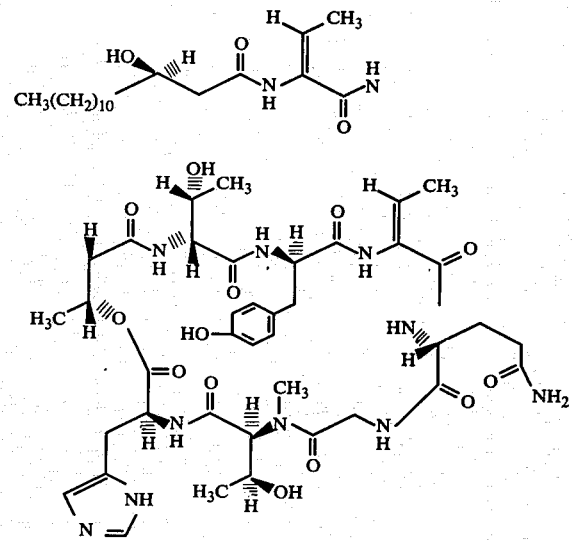

2. Antibiotic 20562, said antibiotic having the following physical properties:
   (a) A melting point of 170°–175° C.;
   (b) A specific optical rotation as measured by the D line of sodium at 26° C. of $-60° \pm 3°$ in 95% pyridine at 0.4% concentration;
   (c) Ultraviolet absorption maxima in methanol at 222 and 280 mμ with $E_{1cm}^{1\%}$ of 268 and 14.8, respectively, and in methanol containing 10% v/v 1N sodium hydroxide, at 240 and 292 mμ with $E_{1cm}^{1\%}$ of 190 and 19.4, respectively;
   (d) An infrared absorption spectrum in mineral oil (Nujol) substantially as shown in FIG. 1;
   (e) a nuclear magnetic resonance spectrum in deuterated dimethylsulfoxide substantially as shown in FIG. 2;
   (f) A molecular formula of C$_{63}$H$_{96}$O$_{21}$N$_{12}$;
   (g) And having a structural formula substantially as follows: